United States Patent [19]

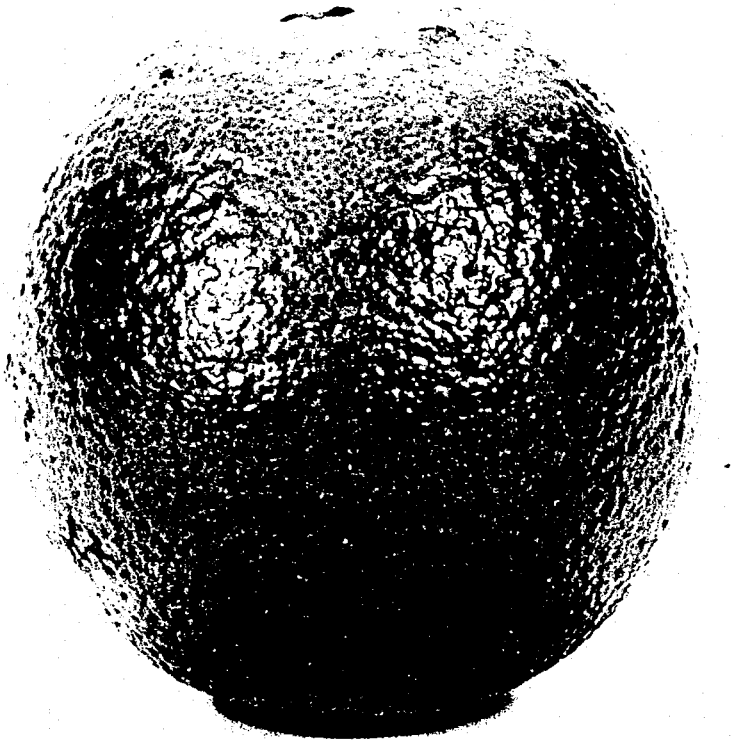

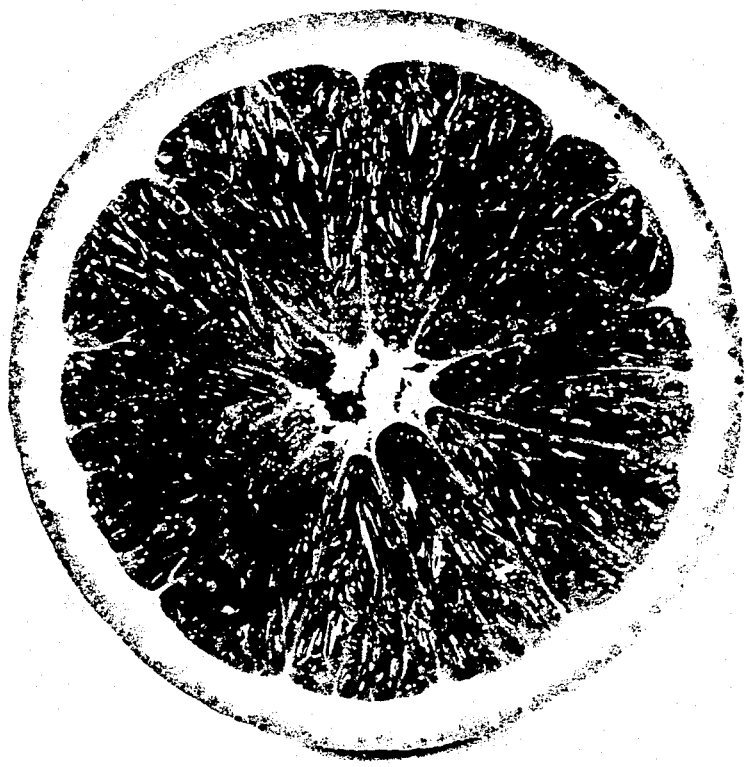

Powell et al.

[11] Patent Number: Plant 6,733

[45] Date of Patent: Apr. 11, 1989

[54] NAVEL ORANGE PLANT NAMED POWELL LATE NAVEL

[76] Inventors: Clive N. Powell; Joyce Powell, both of Delta Road, Curlwaa, New South Wales, Australia

[21] Appl. No.: 122,260

[22] Filed: Nov. 18, 1987

[51] Int. Cl.[4] ..... A01H 5/03

[52] U.S. Cl. ..... Plt./45

[58] Field of Search ..... Plt./45

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of navel orange plant, named Powell Late Navel, characterized by late maturing habits when grown in the inland citrus areas of New South Wales, Australia, and further characterized by its seedless deep orange fruit, the juice of which is characterized by the absence of the bitter taste associated with limionin levels which normally develop after navel oranges are juiced.

2 Drawing Sheets

The invention comprises a new and distinct cultivar of navel orange plant named Powell Late Navel.

The new cultivar is the result of a bud sport observed growing on a tree in a planting of Valencia orange trees budded on to citrange root stocks by the inventor in 1979 in Curlwaa, New South Wales, Australia. The new cultivar was subsequently asexually reproduced by the inventor in Curlwaa, New South Wales, in 1982 by budding on to trifoliate root stock. The resulting tree growth was medium to strong with no bud union abnormalities being noted.

The new cultivar is particularly characterized by late maturing habits when grown in the inland citrus areas of southwest New South Wales, Australia. It is further characterized by the absence of the bitter taste associated with limionin levels which normally develop after navels are juiced, even though the variety contains similar amounts of limionin as Washington navels, namely, 7.3 to 11.6 ppm.

Taste testing of the juice from oranges produced by the new cultivar and stored in a refrigerator for at least five days after each monthly sample confirmed the absence of the bitter taste of off flavors. Further comparative taste tests were carried out using the juice of the Powell Late Navel and the varieties known as Washington Navel and Valencia orange. These tests were carried out by a panel of six people in June, July, August, September, 1986. The order of preference of the panel is as follows, with the first being the most preferred, and the last numbered the least preferred:

1. Powell Late Navel juice 100%.
2. 50% of Powell Late Navel mixed with 50% of Washington Navel juice.
3. 50% of Powell Late Navel juice mixed with 50% Valencia juice.
4. Valencia juice 100%.
5. 50% Valencia juice mixed with 50% Washington Navel juice.
6. Washington Navel juice 100%.

The panel did not detect any off flavors or bitter taste in the first four selections. The fifth and sixth selections were both bitter and off flavored.

The fruit of Powell Late Navel is similar in many respects to the fruit of the cultivar known as Lane Late Navel. However, the rind color of Powell Late Navel is more orange than the rind color of Lane Late Navel, and Powell Late Navel does not develop bitterness or off flavors late in the season. In addition, the season for Powell Late Navel is longer, as will be noted below.

The following description is based upon characteristics of the new cultivar, including produced fruit, as grown in Curlwaa, New South Wales. Color references are to The Royal Horticultural Society Colour Chart (R.H.S.), except where terms of ordinary dictionary significance are used. The fruit was grown in 1986.

FIG. 1 is a color photograph comprising a front perspective view of a typical whole fruit of the new cultivar; and FIG. 2 is a color photograph illustrating a typical cut section of fruit of the new cultivar.

Table 1, attached at the end of the specification, compares total soluble solids, citric acid, Brix°, and sugar to acid ratio for Powell Late Navel and the cultivar Lane Late Navel, throughout the 1986/1987 season. Measurements in each case were carried out on ten fruit samples taken on the date indicated, thereby allowing a standard deviation S.T.D. comparison to check the significant differences.

The dates set forth for Powell Late Navel indicate fruit taken from the original orchard trees, except for the last three months where the fruit was obtained from the first generation trees planted in November, 1982.

The dates set forth for the Lane Late Navel represent fruit taken from the original orchard tree discovered in 1952 by Mr. L. Lane. The season for the Powell Late Navel in southwestern New South Wales is from July to March. The season for the Lane Late Navel in southwestern New South Wales is from June to November.

Citrus Description

Tree: Medium to strong vigor, dense, spreading.

Leaves: Large (90 to 100 mm×50 to 60 mm); variable, lanceolate in form although somewhat variable; apex acute; base narrowed; edges distinctly crenate, marginal oil cells many. Venation distinct. Petioles margined. Mature leaves glossy, dark on upper surface, pale to light green on lower surface. Texture smooth.

Fruit: Large, globose in form; base even; apex slightly depressed, sometimes broadly nippled but usually with large open navel; seedless. Average diameter 75 mm–85 mm, average weight 230–260 g.; rind pebbled, medium-thick (average 4.8 mm). Rind color, orange-deep orange, approximately 26A although color varies. Rind oil cells medium to large. The interior segments are usually 11 to 12 in number, with the segment membranes being thin and tough; pulp vesicles large, medium, long. Juice abundant, evenly distributed in sections, flavor, rich, with acid and sugar well blended.

TABLE 1

| Date of Sample | Powell Late Navel | Lane Late Navel |
|---|---|---|
| | Total soluble solids (kg/ton) | |
| 5/13/86 | 41.03 | — |
| 6/17/86 | 51.56 | 50.98 |
| 7/15/86 | 59.38 | 60.25 |
| 8/13/86 | 62.69 | 65.98 |
| 9/16/86 | 69.58 | 65.12 |
| 10/14/86 | 77.61 | 77.63 |
| 11/12/86 | 84.25 | 70.39 |
| 12/16/86 | 72.12 | 75.37 |
| 1/20/87 | 68.66 | 63.41 |
| 2/18/87 | 67.40 | * no more |
| 3/18/87 | 73.40 | * fruit |
| 4/24/87 | 46.30 | * available |
| | Citric acid (g/100 ml) | |
| 5/13/86 | 1.47 | — |
| 6/17/86 | 1.98 | 1.64 |
| 7/15/86 | 1.10 | 1.29 |
| 8/13/86 | 0.99 | 1.18 |
| 9/16/86 | 0.82 | 0.88 |
| 10/14/86 | 0.73 | 0.75 |
| 11/12/86 | 0.62 | 0.61 |
| 12/16/86 | 0.55 | 0 63 off flavor |
| 1/20/87 | 0.61 | 0.51 off flavor |
| 2/18/87 | 0.28 | * no more |
| 3/18/87 | 0.40 | * fruit |
| 4/24/87 | 0.38 | * available |
| | Brix° | |
| 5/13/86 | 9.6 | — |
| 6/17/86 | 11.6 | 13.2 |
| 7/15/86 | 11.8 | 13.8 |

TABLE 1-continued

| Date of Sample | Powell Late Navel | Lane Late Navel |
|---|---|---|
| 8/13/86 | 12.8 | 13.9 |
| 9/16/86 | 13.5 | 14.8 |
| 10/14/86 | 14.1 | 14.5 |
| 11/12/86 | 13.6 | 14.3 |
| 12/16/86 | 13.3 | 15.4 |
| 1/20/87 | 13.4 | 13.2 |
| 2/18/87 | 14.2 | * no more |
| 3/18/87 | 14.4 | * fruit |
| 4/24/87 | 10.2 | * available |
| | Sugar: acid ratio | |
| 5/13/86 | 6.53 | — |
| 6/17/86 | 5.85 | 8.04 |
| 7/15/86 | 10.72 | 10.69 |
| 8/13/86 | 12.93 | 11.78 |
| 9/16/86 | 16.46 | 16.82 |
| 10/14/86 | 19.32 | 19.33 |
| 11/12/86 | 21.94 | 23.44 |
| 12/16/86 | 24.18 | 24.44 flavor |
| 1/20/87 | 21.97 | 25.88 flavor |
| 2/18/87 | 50.70 | * no more |
| 3/18/87 | 36.10 | * fruit |
| 4/24/87 | 26.80 | * available |
| | Juice Percentage | |
| 5/13/86 | 41.49 | — |
| 6/17/86 | 43.00 | 37.68 |
| 7/15/86 | 49.40 | 42.85 |
| 8/13/86 | 48.26 | 46.66 |
| 9/16/86 | 50.94 | 43.47 |
| 10/14/86 | 54.46 | 52.99 |
| 11/12/86 | 61.39 | 48.81 |
| 12/16/86 | 53.78 | 48.55 off flavor |
| 1/20/87 | 50.79 | 46.97 |
| 2/18/87 | 47.30 | x no more |
| 3/18/87 | 50.70 | x fruit |
| 4/24/87 | 45.16 | x available |

We claim:

1. A new and distinct variety of navel orange plant named Powell Late Navel, as herein described and illustrated.

* * * * *